United States Patent
Selwood et al.

(10) Patent No.: US 7,223,835 B2
(45) Date of Patent: May 29, 2007

(54) VEGF PEPTIDES AND THEIR USE FOR INHIBITING ANGIOGENESIS

(75) Inventors: David Selwood, London (GB); Ian Zachary, London (GB); Haiyan Jia, London (GB); Marianne Lohr, London (GB); Dana Davis, Santa Clara, CA (US)

(73) Assignee: Ark Therapeutics Ltd. (GB)

( * ) Notice: Subject to any disclaimer, the term of this patent is extended or adjusted under 35 U.S.C. 154(b) by 595 days.

(21) Appl. No.: 10/398,616

(22) PCT Filed: Oct. 25, 2001

(86) PCT No.: PCT/GB01/04736

§ 371 (c)(1),
(2), (4) Date: Aug. 6, 2003

(87) PCT Pub. No.: WO01/27136

PCT Pub. Date: Apr. 19, 2001

(65) Prior Publication Data

US 2004/0054143 A1    Mar. 18, 2004

(30) Foreign Application Priority Data

Oct. 25, 2000    (GB) ................................ 0026134.7

(51) Int. Cl.
  *A61K 38/00*    (2006.01)
  *A61K 38/12*    (2006.01)
  *A61K 38/04*    (2006.01)
  *A01N 37/18*    (2006.01)
  *C07K 5/00*    (2006.01)

(52) U.S. Cl. .......................... 530/300; 514/2; 530/317; 530/327; 530/328; 530/329

(58) Field of Classification Search ..................... None
See application file for complete search history.

(56) References Cited

U.S. PATENT DOCUMENTS

2004/0054143 A1 *    3/2004    Selwood et al. ............ 530/350

FOREIGN PATENT DOCUMENTS

WO    WO 99/40197    8/1999
WO    WO 01/27136 A2    4/2001

OTHER PUBLICATIONS

Jouan, Valerie et al. (Aug. 1, 1999) "Inhibition of *In vitro* Angiogenesis by Platelet Factor-4-Derived Peptides and Mechanism of Action" *Blood* 94(3):984-993.
Piosssek, Christine et al. (Feb. 26, 1999) "Vascular Endothelial Growth Factor (VEGF) Receptor II-Derived Peptides Inhibit VEGF" *The Journal of Biological Chemistry* 274(9):5612-5619.
Soker, Shay et al. (Dec. 12, 1987) "Inhibition of Vascular Endothelial Growth Factor (VEGF)-induced Endothelial Cell Proliferation by a Peptide Corresponding to the Exon 7-Encoded Domain of $VEGF_{165}$" *Journal of Biological Chemistry* 272(50):31582-31588.
Bae, Dong-Goo, Gho, Yong-Song, Yoon, Wan-Hee, Chae, Chi-Bom "Arginine-rich Anti-vascular Endothelial Growth Factor Peptides Inhibit Tumor Growth and Metastasis by Blocking Angiogenesis," *The Journal of Biological Chemistry* 275(18): 13588-13596, May 5, 2000, published in the U.S.A.

* cited by examiner

*Primary Examiner*—Robert S. Landsman
(74) *Attorney, Agent, or Firm*—Saliwanchik, Lloyd & Saliwanchik

(57) ABSTRACT

A peptide having part or all of the amino acid sequence QKRKRKKSRYKSWSVP (which is part of VEGF) has the ability to inhibit angiogenesis.

9 Claims, 4 Drawing Sheets

SEQUENCE LISTING

<160> NUMBER OF SEQ ID NOS: 21

<210> SEQ ID NO 1
<211> LENGTH: 16
<212> TYPE: PRT
<213> ORGANISM: Artificial Sequence
<220> FEATURE:
<223> OTHER INFORMATION: Oligopeptide

<400> SEQUENCE: 1

Gln Lys Arg Lys Arg Lys Lys Ser Arg Tyr Lys Ser Trp Ser Val Pro
 1               5                   10                  15

-continued

```
<210> SEQ ID NO 2
<211> LENGTH: 12
<212> TYPE: PRT
<213> ORGANISM: Artificial Sequence
<220> FEATURE:
<223> OTHER INFORMATION: Oligonucleotide

<400> SEQUENCE: 2

Gln Lys Arg Lys Arg Lys Lys Ser Arg Tyr Lys Ser
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Oligopeptide

<400> SEQUENCE: 3

Arg Lys Lys Ser Arg Tyr Lys Ser Trp Ser Val Pro
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Oligopeptide

<400> SEQUENCE: 4

Gln Lys Arg Lys Arg Lys Lys Ser Arg Tyr Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Oligopeptide

<400> SEQUENCE: 5

Gln Lys Arg Lys Arg Lys Lys Ser Arg Tyr
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Oligopeptide

<400> SEQUENCE: 6

Gln Lys Arg Lys Arg Lys Lys Ser Arg
1               5

<210> SEQ ID NO 7
<211> LENGTH: 8
<212> TYPE: PRT
<213> ORGANISM: Artificial Sequence
<220> FEATURE:
<223> OTHER INFORMATION: Oligopeptide

<400> SEQUENCE: 7

Gln Lys Arg Lys Arg Lys Lys Ser
1               5
```

```
<210> SEQ ID NO 8
<211> LENGTH: 7
<212> TYPE: PRT
<213> ORGANISM: Artificial Sequence
<220> FEATURE:
<223> OTHER INFORMATION: Oligopeptide

<400> SEQUENCE: 8

Gln Lys Arg Lys Arg Lys Lys
1               5

<210> SEQ ID NO 9
<211> LENGTH: 6
<212> TYPE: PRT
<213> ORGANISM: Artificial Sequence
<220> FEATURE:
<223> OTHER INFORMATION: Oligopeptide

<400> SEQUENCE: 9

Gln Lys Arg Lys Arg Lys
1               5

<210> SEQ ID NO 10
<211> LENGTH: 11
<212> TYPE: PRT
<213> ORGANISM: Artificial Sequence
<220> FEATURE:
<223> OTHER INFORMATION: Oligopeptide

<400> SEQUENCE: 10

Lys Arg Lys Arg Lys Ser Arg Tyr Lys Ser
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Oligopeptide

<400> SEQUENCE: 11

Arg Lys Arg Lys Lys Ser Arg Tyr Lys Ser
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Oligopeptide

<400> SEQUENCE: 12

Lys Arg Lys Lys Ser Arg Tyr Lys Ser
1               5

<210> SEQ ID NO 13
<211> LENGTH: 8
<212> TYPE: PRT
<213> ORGANISM: Artificial Sequence
<220> FEATURE:
<223> OTHER INFORMATION: Oligopeptide

<400> SEQUENCE: 13

Arg Lys Lys Ser Arg Tyr Lys Ser
1               5

<210> SEQ ID NO 14
```

```
<211> LENGTH: 7
<212> TYPE: PRT
<213> ORGANISM: Artificial Sequence
<220> FEATURE:
<223> OTHER INFORMATION: Oligopeptide

<400> SEQUENCE: 14

Lys Lys Ser Arg Tyr Lys Ser
1               5

<210> SEQ ID NO 15
<211> LENGTH: 6
<212> TYPE: PRT
<213> ORGANISM: Artificial Sequence
<220> FEATURE:
<223> OTHER INFORMATION: Oligopeptide

<400> SEQUENCE: 15

Lys Ser Arg Tyr Lys Ser
1               5

<210> SEQ ID NO 16
<211> LENGTH: 10
<212> TYPE: PRT
<213> ORGANISM: Artificial Sequence
<220> FEATURE:
<223> OTHER INFORMATION: Oligopeptide

<400> SEQUENCE: 16

Lys Ser Arg Tyr Lys Ser Trp Ser Val Pro
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Oligopeptide

<400> SEQUENCE: 17

Ser Arg Tyr Lys Ser Trp Ser Val Pro
1               5

<210> SEQ ID NO 18
<211> LENGTH: 8
<212> TYPE: PRT
<213> ORGANISM: Artificial Sequence
<220> FEATURE:
<223> OTHER INFORMATION: Oligopeptide

<400> SEQUENCE: 18

Arg Tyr Lys Ser Trp Ser Val Pro
1               5

<210> SEQ ID NO 19
<211> LENGTH: 7
<212> TYPE: PRT
<213> ORGANISM: Artificial Sequence
<220> FEATURE:
<223> OTHER INFORMATION: Oligopeptide

<400> SEQUENCE: 19

Tyr Lys Ser Trp Ser Val Pro
1               5

<210> SEQ ID NO 20
<211> LENGTH: 6
```

```
<212> TYPE: PRT
<213> ORGANISM: Artificial Sequence
<220> FEATURE:
<223> OTHER INFORMATION: Oligopeptide

<400> SEQUENCE: 20

Lys Ser Trp Ser Val Pro
1               5

<210> SEQ ID NO 21
<211> LENGTH: 7
<212> TYPE: PRT
<213> ORGANISM: Artificial Sequence
<220> FEATURE:
<223> OTHER INFORMATION: Oligopeptide

<400> SEQUENCE: 21

Arg Lys Arg Lys Lys Ser Arg
1               5
```

VEGF PEPTIDES AND THEIR USE FOR INHIBITING ANGIOGENESIS

This application is a National Stage Application of International Application Number PCT/GB01/04736, published, pursuant to PCT Article 21(2).

FIELD OF THE INVENTION

This invention relates to peptides which are fragments of VEGF (vascular endothelial growth factor) and which have activity of potential benefit in therapy.

BACKGROUND OF THE INVENTION

VEGF is a secreted polypeptide which is essential for formation of the vascular system in embryogenesis and plays a major role in angiogenesis in a variety of disease states. VEGF expression is upregulated by hypoxia and several cytokines in diverse cell types, and elicits multiple biological activities in vivo and in vitro including the differentiation, proliferation, migration and survival of endothelial cells, increased vascular permeability, monocyte migration, and increased endothelial production of the vasodilatory factors NO and prostacyclin. VEGF-induced NO and prostacyclin production are in turn implicated in both angiogenesis and several vascular protective effects of VEGF, including increased permeability, and inhibition of intimal vascular smooth muscle cell hyperplasia and thrombosis.

Human VEGF exists in multiple isoforms of 121, 145, 165, 189 and 206 amino acids, generated by alternative mRNA splicing, of which $VEGF_{121}$, $VEGF_{145}$ and $VEGF_{165}$ are known to be secreted and biologically active forms. Two distinct protein tyrosine kinase receptors for VEGF have been identified, Flt-1 (VEGFR1) and KDR/Flk-1 (VEGFR2). KDR/flk-1 is thought to be the receptor which primarily mediates the mitogenic effects of VEGF in endothelial cells and angiogenesis in vivo; the function of Flt-1 in endothelial cells is unknown. A non-tyrosine kinase transmembrane protein, neuropilin-1 (NP-1), has been identified as an additional receptor for VEGF which specifically binds $VEGF_{165}$, and enhances binding of $VEGF_{165}$ to VEGFR2. The role of NP-1 in mediating biological effects of VEGF is still largely unknown.

SUMMARY OF THE INVENTION

Surprisingly, it has been found that fragments of VEGF are anti-angiogenic. They may have VEGF antagonist activity.

According to the present invention, a peptide has the amino acid sequence

QKRKRKKSRYKSWSVP (SEQ ID No. 1)

wherein any of the Y residues at least may be replaced by an isostere, or a fragment or derivative or homologue thereof; such a peptide inhibits angiogenesis.

The sequence corresponds to amino acids 125 to 140 within VEGF. The invention also encompasses variants of this sequence, in which the novel activity, i.e. the inhibition of angiogenesis, is retained without unexpected structural variation. Thus, the given sequence may include isosteric or homologous replacements or derivatisation that renders the peptide relatively stable.

BRIEF DESCRIPTION OF THE SEQUENCES

SEQ ID NO. 1 is an anti-angiogenic fragment of human VEGF (vascular endothelial growth factor) protein according to the present invention, wherein any of the Y residues at least may be replaced by an isotere. The sequence corresponds to amino acids 125 to 140 within human VEGF.

SEQ ID NO. 2 is the linear dodecapeptide V125–136.

SEQ ID NO. 3 is the linear dodecapeptide V129–140.

SEQ ID NO. 4 is an 11-mer truncated derivative of the 12-mer V125–136 protein.

SEQ ID NO. 5 is a 10-mer truncated derivative of the 12-mer V125–136 protein.

SEQ ID NO. 6 is a 9-mer truncated derivative of the 12-mer V125–136 protein.

SEQ ID NO. 7 is an 8-mer truncated derivative of the 12-mer V125–136 protein.

SEQ ID NO. 8 is a 7-mer truncated derivative of the 12-mer V125–136 protein.

SEQ ID NO. 9 is a 6-mer truncated derivative of the 12-mer V125–136 protein.

SEQ ID NO. 10 is an 11-mer truncated derivative of the 12-mer V125–136 protein.

SEQ ID NO. 11 is a 10-mer truncated derivative of the 12-mer V125–136 protein.

SEQ ID NO. 12 is a 9-mer truncated derivative of the 12-mer V125–136 protein.

SEQ ID NO. 13 is an 8-mer truncated derivative of the 12-mer V125–136 protein.

SEQ ID NO. 14 is a 7-mer truncated derivative of the 12-mer V125–136 protein.

SEQ ID NO. 15 is a 6-mer truncated derivative of the 12-mer V125–136 protein.

SEQ ID NO. 16 is a 10-mer truncated derivative of the 12-mer V129–140 protein.

SEQ ID NO. 17 is a 9-mer truncated derivative of the 12-mer V129–140 protein.

SEQ ID NO. 18 is an 8-mer truncated derivative of the 12-mer V129–140 protein.

SEQ ID NO. 19 is a 7-mer truncated derivative of the 12-mer V129–140 protein.

SEQ ID NO. 20 is a 6-mer truncated derivative of the 12-mer V129–140 protein.

SEQ ID NO. 21 is a 7-mer truncated derivative of the 12-mer V125–136 protein.

BRIEF DESCRIPTION OF THE FIGURES.

FIG. 3A shows VEGE (pg/ml) released from untreated control during 11 days; FIG. 3B shows the untreated control; FIG. 3C shows VEGF; FIG. 3D shows peptide 121–132; FIG. 3E shows VEGF in the presence of peptide 121–132; FIG. 3F shows peptide 125–136 (SEQ ID NO:2); and FIG. 3G is VEGF in the presence of peptide 125–136 (SEQ ID NO:2).

DESCRIPTION OF THE INVENTION

Figure 1:
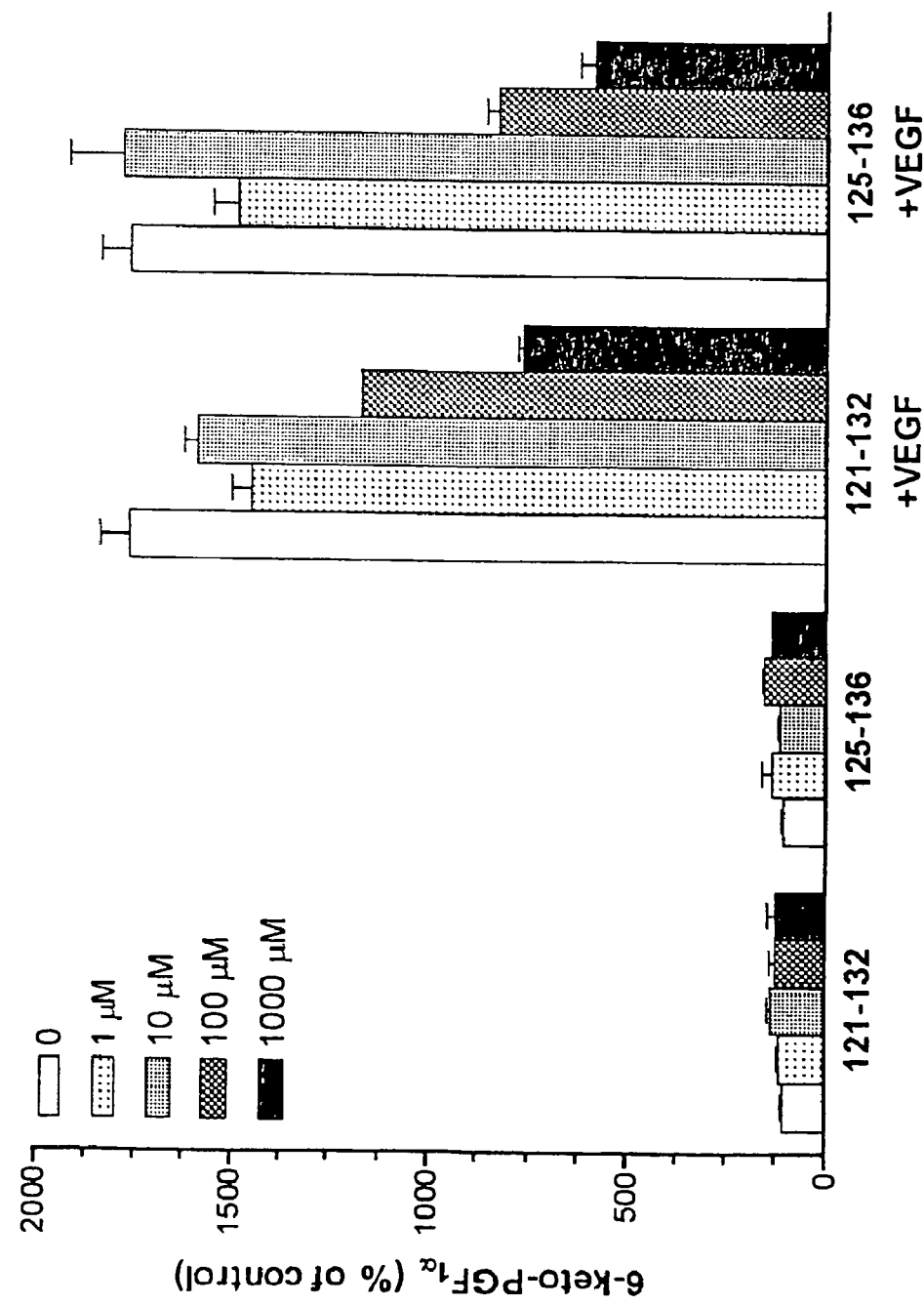
FIG. 1 shows 6-keto-$PGF_{1\alpha}$(% of control) for various μM concentrations of the 121–132 protein, the 125–136 protein, the 121–132 protein+VEGF, and the 125–136 protein+VEGF.

Peptides of the invention may be synthesised by known methods. Examples are given below. They may be formulated and used in known manner. The anti-angiogenic activity associated with the peptides means that they can be used in the treatment of tumours.

A key feature of the amino acid sequence may be the presence and arrangement of basic residues such as K and R. Peptides of the invention preferably comprise 1, 2 or more KK, KR or RK sequences, e.g. spaced by a non-basic residue.

A typical peptide of this invention has at least 4 amino acids. It may have up to 6 or 8 amino acids, but is preferably as short as possible.

A peptide of this invention may be cyclised, e.g. end-to-end or by substituting/introducing 2 Cys residues. Cyclisation procedures are known; see, for example, Tam et al, JACS 113:6657–62 (1991). Other cyclisations, e.g. Mitsunobu or olefin metathesis ring closure, may also be used: The cyclic peptides may exhibit enhanced properties.

As indicated above, peptides of the invention include modifications of the given sequence. Such modifications are well known to those skilled in the art. Isosteric replacements include Abu for Cys (this may be desirable where the peptide should retain an even number of Cys residues for cyclisation), Phe for Tyr and different alkyl/aryl substituents. The shifting of substituents within an amino acid residue, from a C atom to a N atom, to produce peptoids having greater resistance to proteolysis, and other modifications, are known and are included within the scope of this invention.

The anti-angiogenic properties of a peptide of this invention may be determined by the procedure described below. The level of activity is preferably at least as great as that for two linear dodecapeptides that have been the subject of initial testing, i.e. QKRKRKKSRYKS (V125–136; SEQ ID No. 2) and RKKSRYKSWSVP (V129–140; SEQ ID No. 3). Further examples of the invention are SEQ ID Nos. 4 to 21; see also FIG. 2.

The activity of peptides of the invention means that they may be useful in the treatment of diseases in which angiogenesis may have a significant role in pathology. These include angiogenic diseases of the eye such as diabetic retinopathy, or diseases where angiogenesis might be implicated such as ARDS (age-related macular degeneration). Other diseases where angiogenesis may play a significant role are in tumour growth, or in endometriosis, and diseases of the skin such as psoriasis. The peptides may also be useful in the treatment of specific cancers, including Kaposi's sarcoma (which occurs in AIDS patients), malignant melanoma of the skin and eye, and solid malignant tumours of ovary, breast, lung, pancreas, prostate, colon and epidermoid cancers. They may also be used in the treatment of rheumatoid arthritis as an inflammatory condition with a vascular component.

For use in therapy, a peptide of the invention may be formulated and administered by procedures, and using components, known to those of ordinary skill in the art. The appropriate dosage of the peptide may be chosen by the skilled person having regard to typical requirements such as the condition of the subject, the potency of the compound, the route of administration and similar factors.

The following Examples illustrate the invention.

Abbreviations

MBHA, methylbenzhydrylamine; Fmoc, 9-fluorenylmethoxy-carbonyl; Ala, alanine; Arg, arginine; Asn, asparagine; Asp, aspartic acid; Abu, aminobutyric acid; Cys, cysteine; Gln, glutamine; Glu, glumatic acid; Gly, glycine; His, histidine; Ile, isoleucine; Leu, leucine; Lys, lysine; met, methionine; Phe, phenylalanine; Pro, proline; Ser, serine; Thr, threonine; Trp, tryptophan; Tyr, tyrosine; Val, valine; Pbf, 2,2,4,6,7-pentamethyldihydrobenzofuran-5-sulfonyl; Pmc, 2,2,5,7,8-pentamethylchroman-6-sulfonyl; Trt, trityl; tBu, tert-butyl; Boc, butoxycarbonyl; Pybop, benzotriazol-1-yloxytrispryrrolidinophosphonium hexafluorophosphate; NMM, N-methylmorpholine; DCM, dichloromethane; DMF, dimethylformamide; TFA, trifluoroacetic acid; HPLC, high performance liquid chromatography; LC-MS, liquid chromatography mass spectrometry; AAA, amino acid analysis; DMSO, dimethyl sulfoxide; VEGF, vascular endothelial growth factor; TBME, t-butyl methyl ester.

Peptide Syntheses

All peptides were synthesized on an automated AMS 422 Multiple Peptide Synthesizer using the solid phase approach. The Rink Amide MBHA resin (0.59 and 0.68 mmol/g loading) and the N-Fmoc strategy with orthogonal protection (Acm, t-Bu) of the Cys side chains of derivatives to be cyclised were applied. For example, QKRKRKKSRYKS (V125–136; SEQ ID No. 2) and RKKSRYKSWSVP (V129–140; SEQ ID No. 3) were synthesized on a 25 μmolar scale and coupled once with a basic coupling time of 30 minutes. The resin and the amino acid derivatives, Fmoc-Ala-OH.$H_2O$, Fmoc-Arg(Pbf/Pmc)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmnoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro.$H_2O$, Fmoc-Ser(tBu)-OH, Fmoc-Thr(tBu)-OH, Fmoc-Trp(Boc)-OH, Fmoc-Tyr(tBu)-OH and Fmoc-Val-OH were purchased from Calbiochem-Novabiochem UK Ltd. (Nottingham, UK) or Alexis (Nottingham, UK).

Each amino acid was sequentially coupled to the growing peptide chain from the C- to the N-terminus, applying Pybop (Calbiochem-Novabiochem) and NMM (Rathburn Chemicals, Walkerburn, Scotland) as coupling reagents via the active ester method. Removal of the N-Fmoc protecting group was carried out with 20% piperidine in DMF (Rathburn Chemicals) followed by sequential washes with DMF and DCM. Automatic acetylation was carried out after the synthesis of each peptide with a 4-fold excess of acetic acid (0.7 molar, Rathburn Chemicals) based on the substitution of the Rink-Amide-MBHA resin. The coupling reagent, Pybop, NMM and all amino acid derivatives were dissolved in DMF (0.7 M, 4-fold excess based on the substitution of the Rink-Amide-MBHA-resin) except for the amino acids Fmoc-His(Trt)-OH and Fmoc-Phe-OH. These protected amino acid derivatives were dissolved in N-methylpyrrolidone. All solvents used were of HPLC-grade quality.

The peptides were cleaved from the resin with simultaneous deprotection using 90% TFA at room temperature for 3 hours in the presence of 5% thioanisole, 2.5% water and 2.5% ethanedithiol as a scavenger of reactive cations generated. The cleavage mixture was filtered and precipitated in ice-cold TBME. The remaining resin was washed once with the cleavage reagent, filtered and combined with the previous fractions. The precipitates were collected after centrifugation, washed three times with ice-cold TBME and allowed to dry overnight at room temperature. The crude peptides were dissolved in 15% aqueous acetic acid and lyophilised for 2 days (−40° C., 6 mbar).

Purification and Characterisation

The crude peptides were analysed by analytical LC-MS on a Quattro LC Mass Spectrometer from Micromass with a Hewlett-Packard HPLC instrument, model 1100 using analytical reverse-phase columns (column Alltech Hypersil PEP reverse-phase column, 10 nm, $C_8$, 5 μ (250×4.6 mm) 0–50% acetonitrile in 20 minutes. The separations were monitored at a wavelength of 215 nm for the amide bond absorbance with a flow rate of 1 mL/min. The crude peptides were purified by preparative reverse-phase HPLC (Gilson), monitored at 215 nm and eluted at a flow rate of 20 mL/min. The same mobile phase as stated for the LC-MS analysis of the crude peptides was used. The crude peptides were purified using an Alltech Hypersil PEP reverse-phase column, 10 nm, $C_8$, 8 μ (250×22 mm). They were eluted with 0–50% acetonitrile in 20 minutes. The analogues were greater than 95% pure using high performance liquid chromatography (LC-MS) and had the expected amino acid analysis.

Various different gradients were applied for the elution of the peptides which were monitored at 215 nm. The organic phase, acetonitrile, and the aqueous phase both contain 0.1% TFA and 3% 1-propanol. The gradients and flow rates are listed below. The percentage indicates the proportion of the organic phase. 0–50% in 20 min, flow rate of 1 mL/min.

Inhibition of VEGF-stimulated PGI2 Production by Peptides

Confluent HUVECs in 12-well plates were pre-incubated with peptides V-125–136 and V129–140 at the indicated concentrations for 30 min and then either incubated for a further 30 min with no further addition or were exposed to VEGF (25 ng/ml) for 1 h. Some cells were incubated without peptides either in the absence (C, control) or presence of 25 ng/ml VEGF. The supernatants were collected and 6-keto-prostaglandin $F_{1\alpha}$ was measured by enzyme immunoassay. The results are shown in FIG. 1, where bars represent mean percentages: ±SEM of the unstimulated control level of 6-keto-prostaglandin $F_{1\alpha}$ (100%) obtained from duplicate determinations. Similar results were obtained from two independent experiments.

$^{125}$I-VEGF$_{165}$ Binding Assay

Confluent HUVECs in 24-well plates were washed twice with PBS and incubated at 4° C. with various concentrations of peptides diluted in binding medium (DMEM, 25 mM HEPES, pH 7.3 containing 0.1% BSA) and in the presence of 0.03 nM or 0.1 nM $^{125}$I-VEGF$_{165}$ (1200–1800 Ci/mmol, Amersham). After a 2 h incubation at 4° C., the cells were washed 4 times with cold PBS and then lysed with 0.25 M NaOH, 0.5% SDS, and the bound radioactivity of the lysates was measured. Non-specific binding was determined in the presence of a 100-fold excess of unlabelled VEGF. Specific binding was calculated by subtracting the non-specific binding from the total binding. All binding experiments were performed in triplicate.

Figure 2:
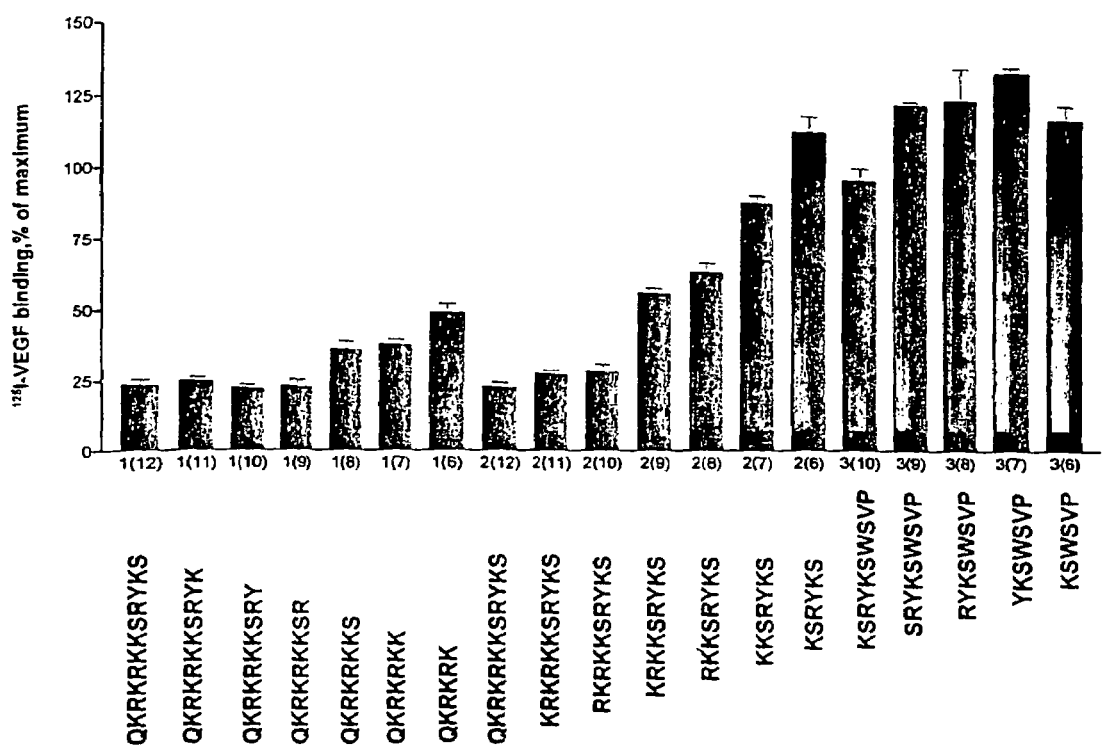
FIG. 2 shows the percent of maximum $^{125}$I-VEGF binding for SEQ ID NOs:2 and 4–20. Results show that the 10-mer RKRKKSRYKS (SEQ ID NO:11) and the 9-mer QKRKRKKSR (SEQ ID NO:6) have similar activity to the 12-mer.

A series of truncated derivatives of the 12-mer V125–136 has been tested. Results show that the 10-mer RKRKKSRYKS (SEQ ID NO:11) and the 9-mer QKRKRKKSR (SEQ ID NO:6) have similar activity to the 12-mer (FIG. 2). This suggests that N- and C-terminal truncations may not affect activity, and that the minimal sequence required for bioactivity is the 7-mer RKRKKSR (SEQ ID NO:21).

In vitro Angiogenesis Assay

Figure 3:
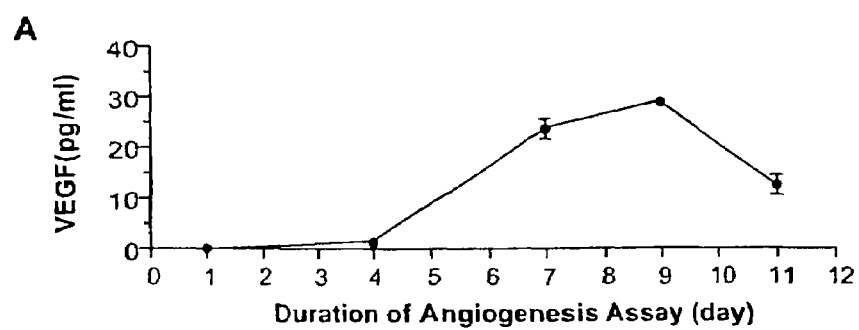
FIGS. 3A–G show the results of an angiogenesis assay.
Figure 3:
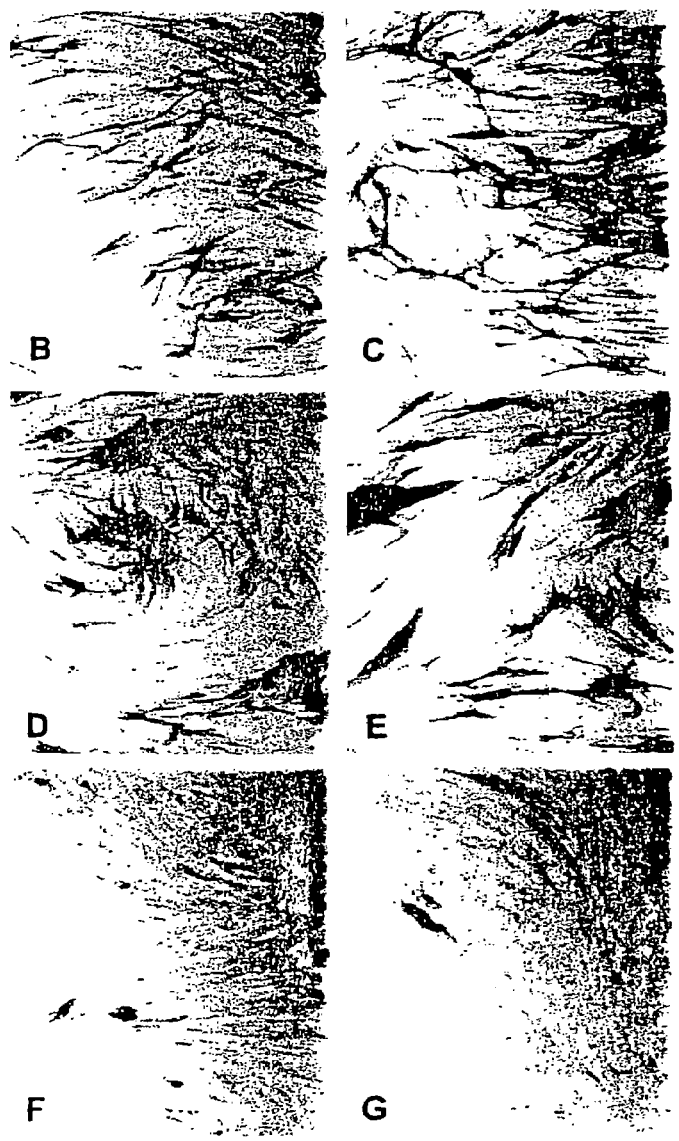

An in vitro angiogenesis assay based on human endothelial cell-derived tubule formation (TCS Biologicals) in a co-culture with human fibroblasts was used to investigate the effects of selected peptides on angiogenesis. The peptides, together with VEGF and other factors were added at the start of the experiment and at each medium change at days 4, 7 and 9. At day 11, the cultures were fixed with 70% ethanol for 30 min at room temperature and subsequently subjected to immunostaining for the endothelial cell adhesion molecule CD31. Fixed cells were incubated with the primary antibody (mouse anti-human CD31) for 1 h at 37° C., washed 3 times in blocking buffer (PBS containing 1% BSA), and then incubated with the secondary antibody (goat anti-mouse IgG conjugated to alkaline phosphatase) for 1 h at 37° C. After 3 washes in distilled water, the cells were finally incubated with the substrate solution for 10 min at 37° C. Immunostaining was observed and photographed using an inverted Zeiss microscope (Axiovert CFL25) fitted with a ×4 objective lens. In each experiment control wells with either VEGF alone, VEGF plus 20 μM suramin, a known inhibitor of VEGF-induced angiogenesis, and no addition were included. Some results are shown in FIG. 3, where. A, VEGF released from untreated control during 11 days, measured by specific immunoassay; B, untreated control; C, VEGF; D, peptide 121–132; E, VEGF in the presence of peptide 121–132; F, peptide 125–136; and G, VEGF in the presence of peptide 125–136.

Figure 4:
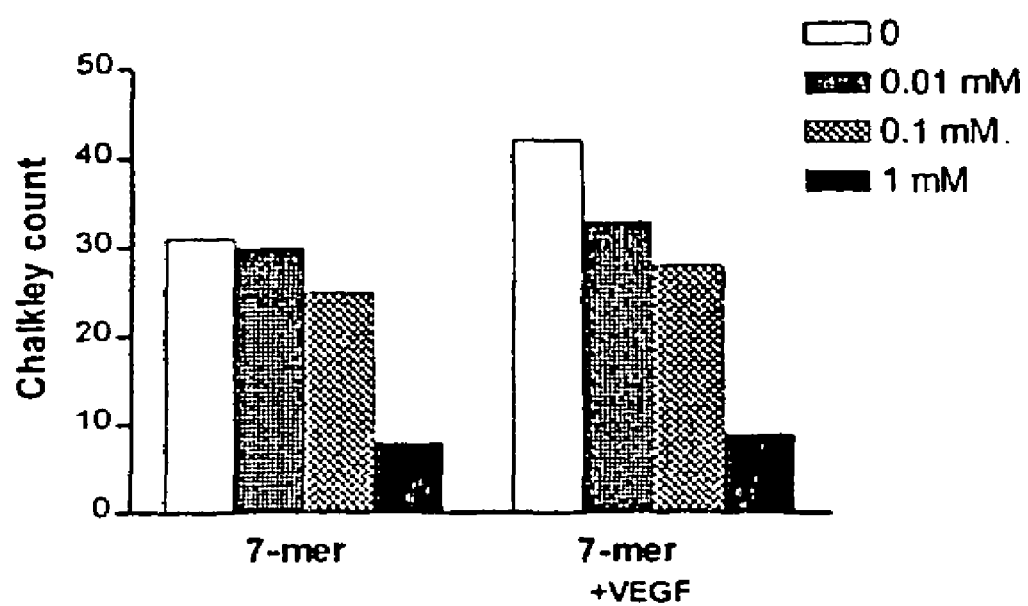
FIG. 4 shows the Chalkley count for the 7-mer RKRKKSR (SEQ ID NO:21) and the 7-mer SEQ ID NO:21+VEGF.

Further results of this assay are shown in FIG. 4. These results are for the 7-mer RKRKKSR (SEQ ID No. 21), and show that it inhibits angiogenesis with similar potency to the 12-mer.

The invention claimed is:

1. An isolated peptide that inhibits angiogenesis and has the following amino acid sequence

QKRKRKKSRYKSWSVP wherein the Y residue may be replaced by tyrosine; or a fragment of said sequence that comprises at least RKRKKSR and which inhibits angiogenesis.

2. The peptide according to claim 1, which has 7 or 8 amino acids.

3. The peptide according to claim 1, in cyclic form.

4. A pharmaceutical composition comprising a peptide that inhibits angiogenesis and has the following amino acid sequence

QKRKRKXSRYKSWSVP wherein the Y residue may be replaced by tyrosine; or a fragment of said sequence that comprises at least RKRKKSR and which inhibits angiogenesis; and a pharmaceutical carrier.

5. The pharmaceutical composition, according to claim 4, wherein said peptide has 7 or 8 amino acids.

6. The pharmaceutical composition, according to claim 4, wherein said peptide is in cyclic form.

7. A method for inhibiting angiogenesis wherein said method comprises administering to a patient in need of such treatment an effective amount of a peptide that inhibits angiogenesis and has the following amino acid sequence

QKRKRKKSRYKSWSVP wherein the Y residue may be replaced by tyrosine; or a fragment of said sequence that comprises at least RKRKKSR and which inhibits angiogenesis.

8. The method, according to claim 7, wherein said peptide has 7 or 8 amino acids.

9. The method, according to claim 7, wherein said peptide is in cyclic form.

* * * * *